United States Patent
Sato et al.

(10) Patent No.: US 7,022,354 B1
(45) Date of Patent: Apr. 4, 2006

(54) PROCESS FOR PRODUCING FERMENTATION PRODUCT

(75) Inventors: Masahide Sato, Yaizu (JP); Shingo Umemoto, Yaizu (JP)

(73) Assignee: Sapporo Breweries Limited, Tokyo (JP)

( * ) Notice: Subject to any disclaimer, the term of this patent is extended or adjusted under 35 U.S.C. 154(b) by 9 days.

(21) Appl. No.: 09/763,864

(22) PCT Filed: Jun. 30, 2000

(86) PCT No.: PCT/JP00/04355

§ 371 (c)(1),
(2), (4) Date: May 23, 2001

(87) PCT Pub. No.: WO01/02534

PCT Pub. Date: Jan. 11, 2001

(30) Foreign Application Priority Data

Jun. 30, 1999 (JP) ................................. 11/186117

(51) Int. Cl.
*C12C 11/02* (2006.01)
(52) U.S. Cl. ........................... 426/11; 426/15; 426/16; 426/28; 426/29
(58) Field of Classification Search ................ 426/11, 426/15, 16, 28, 29
See application file for complete search history.

(56) References Cited

FOREIGN PATENT DOCUMENTS

| JP | 63-44880 | | 2/1988 |
|---|---|---|---|
| JP | 3-164188 | | 7/1991 |
| JP | 6197749 | * | 7/1994 |
| JP | 33346811 | * | 7/1994 |
| JP | 7-123969 | | 5/1995 |
| JP | 7-184638 | | 7/1995 |
| JP | 8-266287 | | 10/1996 |
| JP | 41075883 | * | 3/1999 |
| JP | 3346811 | * | 11/2002 |
| WO | WO 95/07343 | | 3/1995 |
| WO | WO 99/11751 | | 3/1999 |

OTHER PUBLICATIONS

Szlavko, Jnl. of Amer. Soc. of Brewing Chemists, 34 (2) pp. 59-60, 1976.*

J.C. Ogbonna, et al., Process Biochemistry, vol. 31, No. 8, pp. 737-744, "Development of a Method for Immobilization of Non-Flocculating Cells in Loofa (Luffa Cylindrica)", 1996.

Osamu Kobayashi, et al., Journal of Bacteriology, vol. 180, No. 24, pp. 6503-6510, "Region of Flo1 Proteins Responsible for Sugar Recognition", Dec., 1998.

(Continued)

*Primary Examiner*—Milton I. Cano
*Assistant Examiner*—Sarah L Kuhns
(74) *Attorney, Agent, or Firm*—Oblon, Spivak, McClelland, Maier & Neustadt, P.C.

(57) ABSTRACT

A process for producing a fermentation product by effecting fermentation with the use of a bioreactor having an immobilized microorganism located therein, characterized in that a non-flocculent yeast is employed as the microorganism.

30 Claims, 8 Drawing Sheets

OTHER PUBLICATIONS

J.R. Johnston, et al., Yeast Genetics, Fundamental and Applied Aspects, pp. 205-207, "Genetic Control of Flocculation", 1983.

U.S. Appl. No. 10/067,241, filed Feb. 7, 2002, pending.

U.S. Appl. No. 09/763,864, filed May 23, 2001, pending.

F. H. White, et al., Journal of the Institute of Brewing, vol. 84, No. 4, XP-002272874, pp. 228-230, "Continuous Fermantation by Immobilized Brewers Yeast", 1987.

I. Virkajarvi, et al., Journal of the Institute of Brewing, vol. 106, No. 5, XP-002272875, pp. 311-318, "Primary Fermentation With Immobilized Yeast: Some Effects of Carrier Materials on the Flavour o the Beer", 2000.

S. Unemoto, et al., Technical Quarterly-Master Brewers Association of the Americas, vol. 35, No. 2, XP-002097635, pp. 58-61, "Primary Fermentation With Immobilized Yeast in a Fluidized Bed Reactor", 1998.

* cited by examiner

PROCESS FOR PRODUCING FERMENTATION PRODUCT

TECHNICAL FIELD

The present invention relates to a method of making a fermentation product; and, more specifically, to a method of making a fermentation product by carrying out fermentation by use of a bioreactor within which an immobilized microorganism is disposed.

BACKGROUND ART

As biotechnology advances, the making of fermentation products by use of bioreactors utilizing immobilized microorganisms is under study in the fields of brewing for malt alcohol beverages (beers), wines, sake, vinegar, soy sauce, and the like. When a bioreactor is used as such, the following are expected:

1) Since a high concentration of yeast is immobilized to carry out fermentation, the brewing is completed rapidly, so that the brewing period can be shortened, whereby the number of manufacturing tanks and the cost of construction can be lowered.

2) Since continuous fermentation is possible, it is unnecessary to charge and collect yeast.

Conventionally, when a beer or the like is manufactured by use of a bioreactor, however, the amount of amino acids and diacetyl (DA) has become greater, and the amount of ester has become smaller in the product as compared with a product manufactured by a traditional batch fermentation method. As a result, the product obtained by use of the bioreactor has been problematic in that it is disadvantageous in flavor, and this problem has been remarkable in particular when the bioreactor is used for primary fermentation (main fermentation).

For overcoming such a problem, studies have conventionally been carried out. Japanese Patent Application Laid-Open Gazette No. HEI 7-123969 discloses a method in which a fermentation liquid is circulated in a continuous fermentation method using a fluidized bed type reactor. Though the consumption of amino acids in the fermentation process is ameliorated by this method, the amount of diacetyl which causes raw odor or immature odor is not lowered sufficiently, whereby the resulting product still has room for improvement in terms of flavor. Also, manufacturing methods in bioreactors including this method have been problematic in that the number of floating yeast cells upon the end (completion) of primary fermentation is small in general, the fermentation rate in the process of fermentation is unstable, and they are hard to control.

Meanwhile, it has conventionally been known that yeast for making a fermentation product such as beer is required to have flocculation ability (agglutinability) to a certain extent. Here, flocculation ability refers to a property in which yeast cells flocculate as a mass upon the end of fermentation and are separated from the liquid so as to float up or sediment. If the flocculation ability is too high, then the flocculation occurs at an earlier stage, so that the contact between the fermentation liquid and yeast is broken, whereby fermentation becomes insufficient. If the flocculation ability is too low, by contrast, then yeast floats in the liquid for a long time, so that the amount of recovery of yeast decreases, which takes unnecessary time and labor for separating and collecting yeast by centrifuge or the like, for example. Therefore, it has conventionally been common knowledge to use yeast having a certain degree of flocculation ability (flocculent yeast) for making a fermentation product. Such flocculent yeast (agglutinative yeast) is used in the above-mentioned method disclosed in Japanese Patent Application Laid-Open Gazette No. HEI 7-123969 as well.

In view of the above-mentioned problems in the prior art, it is an object of the present invention to provide a method in which, when making a fermentation product by use of a bioreactor utilizing an immobilized microorganism, the fermentation rate in the fermentation process can be held constant, and the number of floating yeast cells upon the end of fermentation can stably be maintained at a level higher than the conventional one, whereby, when making a malt alcohol beverage by use of a bioreactor in particular, the amount of diacetyl in the fermentation liquid and final product can be lowered sufficiently and so forth, so as to improve the flavor of final product.

DISCLOSURE OF THE INVENTION

The inventors have repeated diligent studies in order to achieve the above-mentioned object, and have found that non-flocculent yeast (nonagglutinative yeast) can be employed contrary to the conventional knowledge when using a bioreactor utilizing an immobilized microorganism, since it is not necessary to separate and collect yeast, so that the fermentation rate in the fermentation process becomes constant, the number of floating yeast cells upon the end of fermentation is stably maintained at a level further preferable for secondary fermentation (after-fermentation), the amount of diacetyl in the fermentation liquid and final product sufficiently decreases in the case using such a bioreactor for primary fermentation of a malt alcohol beverage in particular, and so forth, whereby the flavor of product improves. Thus, the present invention has been accomplished.

Namely, the method of making a fermentation product in accordance with the present invention is a method of making a fermentation product by using a bioreactor within which an immobilized microorganism is disposed, wherein non-flocculent yeast is used as the microorganism.

The malt alcohol beverage of the present invention is made by the method of the present invention.

BEST MODES FOR CARRYING OUT THE INVENTION

Figure 1:
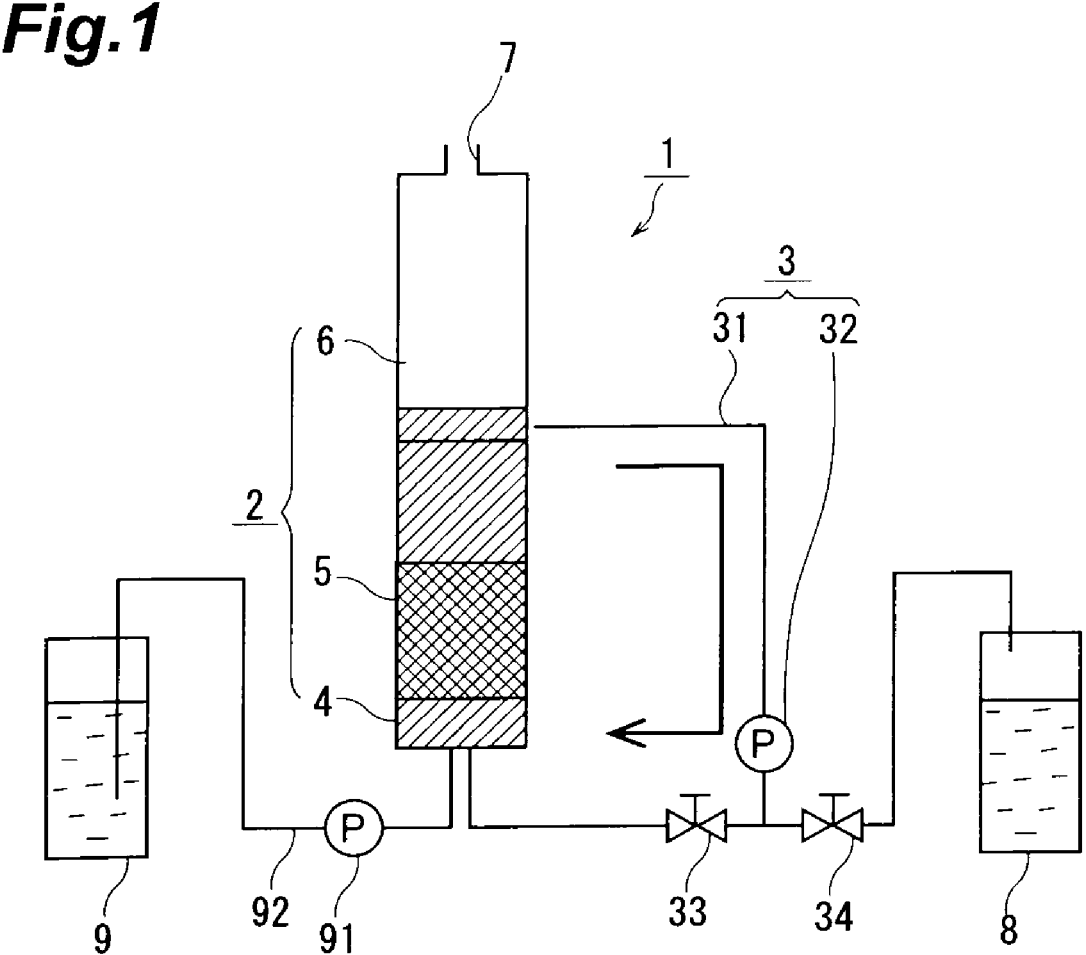
FIG. 1 is a schematic diagram of an example of fluidized bed type reactor suitable for the present invention.

In the following, preferred embodiments of the present invention will be explained in detail.

The present invention is a method of making a fermentation product by carrying out fermentation by using a bioreactor within which an immobilized microorganism is disposed, wherein non-flocculent yeast is used as the microorganism.

First, the yeast and its immobilizing carrier in accordance with the present invention will be explained. Any yeast can be used in the present invention as long as it is non-flocculent as will be explained later, and non-flocculent ones are selected from yeast species corresponding to the aimed fermentation product. For example, as yeast used for making a liquor, non-flocculent ones are selected from so-called liquor yeast species which produce alcohol, carbonic acid gas, and the like by metabolizing a brewing material liquid. Specifically, non-flocculent ones are selected from *Saccharomyces cerevisiae*, *Saccharomyces uvarum*, and the like. Examples of such liquor yeast include non-flocculent beer yeast, non-flocculent wine yeast, and non-flocculent sake yeast. For example, non-flocculent beer yeast may be used so as to make a malt alcohol beverage such as beer.

Here, flocculation ability refers to a property in which yeast cells dispersed in a fermentation process flocculate (aggregate) so as to attach and bind to each other at cell surfaces, thereby forming a floc. Bottom fermentation yeast species used for normal beer production include strains which tend to be rapidly separable from within a fermentation liquid by flocculating (aggregating) their cells to form a floc, and strains which are hard to flocculate and are likely to disperse and float for a relatively long period of time. The former are referred to as "flocculent yeast," whereas the latter are referred to as "non-flocculent yeast (also known as dust-like yeast)."

While it has been reported that such flocculation ability of yeast is essentially a genetic characteristic of yeast itself and is controlled by Lg-FLO 1 gene existing at a position corresponding to the VIII chromosome of *Saccharomyces cerevisiae* (Japanese Patent Application Laid-Open Gazette No. HEI 8-266287), it may also be influenced by water for brewing, materials, malt compositions, malt aeration conditions, yeast culture conditions, fermentation vessels, handling of yeast, and the like, and the strength of flocculation ability may vary as the fermentation process proceeds. Thus, the strength of flocculation ability varies depending on yeast strains, and the same species of yeast may include non-flocculent and flocculent ones depending on strains. Therefore, it is preferred in the present invention that a non-flocculent strain be selected by the following method and the like, so as to use non-flocculent yeast derived from this strain. In particular, it is preferred to use such non-flocculent yeast alone.

An example of methods for measuring the flocculation ability of yeast so as to select non-flocculent yeast to be used for the method of the present invention as such is one described in YEAST GENETICS: FUNDAMENTAL AND APPLIED ASPECTS, 205–224 (1983). Specifically, the following method is preferred.

Namely, 0.6 g of yeast (one separated by precipitation upon centrifuge at 3000×g for 10 minutes at the time when fermentation is completed) is added to 20 ml of tap water, so as to yield a yeast suspension. To 9 ml of this yeast suspension, 1 ml of 0.5-M acetic acid buffer solution at pH 4.5 including 1500 ppm of calcium ion is added. The resulting mixture is hand-shaken up and down, for example, so as to uniformly stir it as a whole. Then, the mixture is left to stand still for 5 minutes at room temperature.

Thereafter, the degree of agglutination is visually inspected (by the naked eye), and is evaluated according to the following four criteria:

0: Non-flocculent (No boundary is seen between the liquid and floc by the naked eye, and neither flocculation (aggregation) nor sedimentation of yeast is observed.)

1: Weakly Flocculent (Though no boundary can be seen between the liquid and floc by the naked eye, flocculation or sedimentation of a part of yeast is observed.)

2: Mildly Flocculent (A boundary can be seen between the liquid and floc by naked eye, and flocculation or sedimentation of yeast is observed.)

3: Strongly Flocculent (Yeast substantially completely flocculates and sediments, and the supernatant becomes substantially completely clear.)

It is preferred in the present invention that a non-flocculent strain satisfying the non-flocculent condition (level 0) in the above-mentioned evaluation criteria be selected, and non-flocculent yeast derived from this strain be used. In particular, it is preferable to use such non-flocculent yeast alone.

Thus, contrary to the conventional knowledge, the method of the present invention uses non-flocculent yeast derived from the non-flocculent strain, so that yeast is fully prevented from flocculating within the bioreactor in the process of fermentation and thereby sedimenting and precipitating, whereby the fermentation rate is held constant, and the number of floating yeast cells upon the end of fermentation is stably maintained at a level higher than that in the case where conventional flocculent yeast is used. In the case where the method of the present invention is employed in primary fermentation of a malt alcohol beverage in particular, the amount of diacetyl in the fermentation liquid upon the end of primary fermentation is sufficiently lowered since the number of floating yeast cells upon the end of primary fermentation improves, and diacetyl is further efficiently reduced in secondary fermentation, so that the amount of diacetyl in the final product sufficiently decreases, thus lowering the resulting immature odor component, whereby the flavor of product improves.

Without being restricted in particular, various kinds of carriers can be used as a carrier for immobilizing the above-mentioned non-flocculent yeast. In particular, carriers comprising chitin-chitosan, alginic acid, carrageenan are preferable. Among others, chitosan type beads (carriers made from chitin-chitosan obtained by actylation of chitosan) are preferable. Since chitosan type beads are hydrophilic and porous, carbonic acid gas is easily let out therefrom. Also, they are hard to wear, and their fluidity is favorable since their density approximates that of the material liquid. Further, the chitosan type beads can hold a large amount of microorganisms, thereby tending to shorten the fermentation time more. Also, since microorganisms are adsorbed and immobilized by the chitosan type beads relatively mildly, their growth and desorption become easier, and dead cells are kept from continuously existing within the carrier as in a collective carrier.

Any method can be used for the sterilization carried out before immobilizing non-flocculent yeast onto such a carrier. Preferred are high-pressure sterilization method, sterilization method using caustic soda, sterilization method using steam, and the like. Also, the method of immobilizing non-flocculent yeast onto the carrier is not restricted in particular. While its examples include one in which the carrier is added to a yeast suspension, and then the mixture is stirred or the liquid is circulated, other known methods may be used as well.

The bioreactor in accordance with the present invention will now be explained. The bioreactor in accordance with the present invention is one within which the immobilized microorganism (non-flocculent yeast immobilized to the carrier) is disposed, and the material liquid and immobilized microorganism come into contact with each other, whereby fermentation is carried out. Examples of such a bioreactor include, in terms of their types, complete mixed vessel type reactors, packed bed type reactors, film type reactors, fluidized bed type reactors, and lateral reactors. For fermentation in which alcohol and carbonic acid gas are generated upon metabolizing a brewing material, such as primary fermentation of malt alcohol beverages, it is preferable to use fluidized bed type reactors which easily let the gas out of the system.

Preferably, such a fluidized bed type reactor comprises a fluidized bed section within which an immobilized microorganism is disposed, and a liquid circulating section for extracting a part of the fermentation liquid from the downstream side of the fluidized bed section and returning it to the upstream side of the fluidized bed section. FIG. 1 is a schematic diagram showing an example of the fluidized bed type reactor suitable for the present invention.

The fluidized bed type reactor 1 shown in FIG. 1 comprises a reaction tank 2 and a liquid circulating section 3. The reaction tank 2 is constituted, successively from the upstream side thereof, by a rectifying section 4, a fluidized bed section 5, and an empty tube section 6, whereas the downstream end portion of the reaction tank 2 is provided with a gas outlet section 7. The liquid circulating section 3 is constituted by a pipe 31 connected to the downstream side of the fluidized bed section 5 and to the upstream side of the fluidized bed section 5 (to the rectifying section 4 in FIG. 1), a pump 32, and a valve 33. Further, the pipe 31 branches off on its way, so as to connect with a product tank 8 by way of a valve 34. Also, a material liquid tank 9 is connected to the upstream end portion of the reaction tank 2 by way of a pipe 92 having a pump 91.

The fluidized bed section 5 is a section within which the carrier having immobilized the microorganism is disposed, whereas the liquid circulating section 3 is a section for extracting from the downstream side of the fluidized bed section 5 a part of the fermentation liquid (material liquid) supplied to the reaction tank 2 and returning it to the upstream side of the fluidized bed section 5 of the reaction tank 2. In the reactor 1 shown in FIG. 1, the extracted fermentation liquid (material liquid) is returned into the reaction tank 2 from the rectifying section 4, where the flow of introduced liquid is rectified. The empty tube section 6 is a section where the carbonic acid gas and fermentation liquid generated during fermentation are separated from each other as a gas and a liquid; and specifically is the part from the liquid surface to the gas outlet section 7 in the upper portion of the reaction tank 2. The gas such as carbonic acid gas isolated in the empty tube section 6 is let out of the vessel by way of the gas outlet section 7.

In the fluidized bed type reactor 1 shown in FIG. 1, the carrier having immobilized the microorganism is disposed in the fluidized bed section 5, and the material liquid is supplied to the rectifying section 4 from the material liquid tank 9 by use of the pump 91, so as to carry out fermentation. Then, a part of the fermentation liquid (material liquid) is extracted from the downstream side of the fluidized bed section 5 by use of the pump 32 of liquid circulating section 3 and is returned to the upstream side of the fluidized bed section 5 (to the rectifying section 4 in FIG. 4) in the reaction tank 2, whereby fermentation is carried out while forming a fluidized bed. The carbonic acid gas generated during fermentation is let out of the vessel via the gas outlet section 7 by way of the empty tube section 6 without staying within the fluidized bed, since the fermentation liquid is circulated and so forth. While the liquid space velocity (linear velocity of fluid per unit volume of fluidized bed) can be changed depending on the density of the carrier having immobilized the microorganism, it is preferably 1 to 20 cm/min, more preferably 1 to 12 cm/min.

It is preferred in the fluidized bed type reactor 1 shown in FIG. 1 that, secondary fermentation is completed, the fermented liquid including a fermentation product be taken out from the reactor 1 into the product tank 8 by way of the pump 32 and valve 34, and a new material liquid be supplied from the material liquid tank 9 to the reactor 1 by use of the pump 91, so as to repeatedly carry out the fermentation. Namely, after the end of fermentation, the circulation is stopped and, concurrently with or immediately after the fermented liquid is extracted out of the reactor 1, a new material liquid is supplied to the reactor 1, so as to repeatedly carry out the fermentation.

While the reactor 1 can be operated by any of batch type, repeated batch type, and continuous type methods, repeated batch type fermentation is preferable for yielding a product having a better flavor in a short time. The repeated batch type operation tends to yield a better flavor since the microorganism is grown and renewed during fermentation, while the physiological state and growth period of microorganic cells, the microorganic cell distribution within the reactor 1, and the like are similar to those in the batch type operation, which is a traditional method of making liquors.

Any material for making a fermentation product may be used as long as it is suitable for fermentation caused by the nonagglutinative yeast employed, and known materials can be used at will. For example, malts, fruit juices, sugar liquids, cereal saccharified liquids, and the like are normally used alone or in combination as appropriate in the making of liquors. Also, appropriate nutrients and the like may be added thereto when necessary.

Fermentation conditions are not different from known conditions in essence. For example, the fermentation temperature is normally 15° C. or lower, preferably 8 to 10° C., in the case of brewing malt alcohol beverages; whereas it is normally 20° C. or lower, preferably 15 to 20° C., in the case of brewing wines.

Examples of fermentation products which can be made by the method of the present invention include products in various brewing fields such as malt alcohol beverages, wines, sake, vinegar, and soy sauce, among which liquors such as malt alcohol beverages, wines, and sake are preferred. In particular, malt alcohol beverages such as beer are preferable since their flavor is improved by the present invention.

EXAMPLES

In the following, the contents of the present invention will be explained in more detail with reference to Examples and Comparative Examples. However, the present invention is not restricted by these Examples at all.

In the following Examples and Comparative Examples, flocculent strains (A-1, A-2) and non-flocculent strains (NA-1, NA-2, NA-3, NA-4, NA-5) selected, according to the above-mentioned methods and criteria, from beer yeast (*Saccharomyces cervisiae* or the like) actually used in the site of manufacture were used. Table 1 shows the results of evaluation of their flocculation ability. For reference, the results of similar evaluation of flocculation ability concerning type cultures NCYC-No. 203 and NCYC-No. 985 in NCYC (National Collection of Yeast Cultures (United Kingdom)) are also shown in Table 1.

TABLE 1

RESULT OF FLOCCULATION ABILITY EVALUATION FOR BEER YEAST

| YEAST | | RESULT |
|---|---|---|
| STRAINS USED IN THIS TEST | A-1 | 2 |
| | A-2 | 2 |
| | NA-1 | 0 |
| | NA-2 | 0 |
| | NA-3 | 0 |
| | NA-4 | 0 |
| | NA-5 | 0 |
| TYPE CULTURE | NCYC-No. 203 | 2 |
| | NCYC-No. 985 | 0 |

Examples 1 and 2 and Comparative Example 1

Using the fluidized bed type bioreactor (total volume: 180 ml) shown in FIG. 1, the primary fermentation was carried out by the above-mentioned repeated batch fermentation (repeated batch type) under the following conditions. Then, thus obtained fermentation liquid was subjected to a floating yeast cell counting test which will be explained later.

Primary Fermentation Conditions

Carrier: chitosan type beads (Chitopearl HP manufactured by Fuji Spinning Co., Ltd.)

Scale: 50 ml of carrier, 100 ml of wort

Strains Used: A-1 (Comparative Example 1), NA-1 (Example 1), NA-2 (Example 2)

Yeast Immobilizing Method: Yeast is immobilized as being brought into contact with the carrier for 2 days while being circulated according to a conventional method (2.4 g of sludge yeast with respect to 50 ml of carrier).

Flow Rate: about 1 ml/min

Fermentation temperature: constantly 8° C.

Fermentation Time: 48 hours/batch

Batch number of Fermentation times: 10

Wort Used: wort (malt) adjusted to yield a sugar index of 11% Plato.

Floating Yeast Cell Counting Test

After the end of each primary fermentation process, the number of floating yeast cells in the fermentation liquid was counted by use of a Thoma blood cell counting plate. The obtained results are shown in Table 2 and FIG. 2. Here, first several repeated fermentation processes were excluded from the counting since they correspond to the acclimatization period of yeast in the carrier (ditto in the following).

Figure 2:
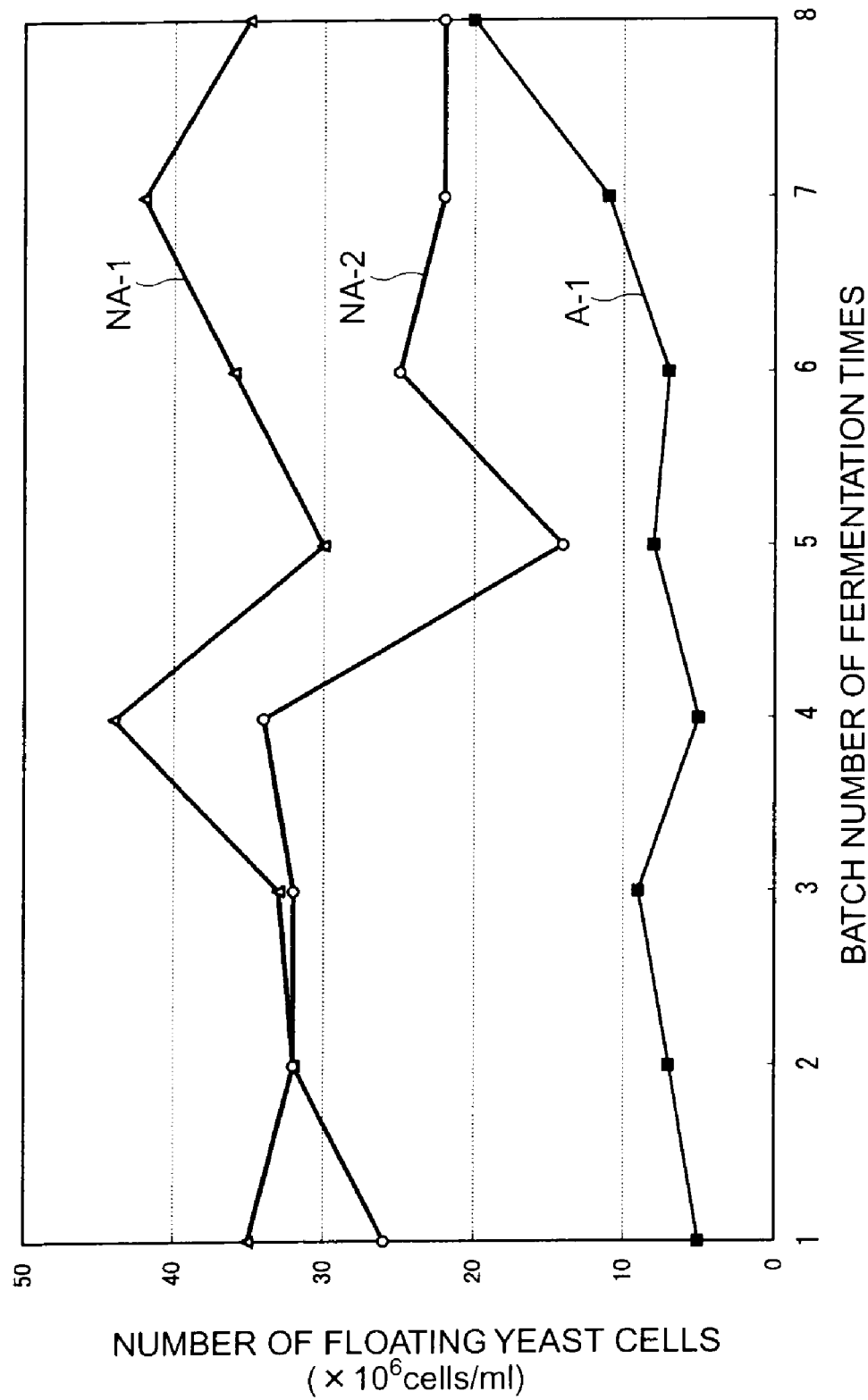
FIG. 2 is a graph showing relationships between the batch number of fermentation times (the number of continuous fermentation processes) and the number of floating yeast cells.

As can be seen from the results shown in Table 2 and FIG. 2, when non-flocculent strains were used under the above-mentioned conditions, the number of floating yeast cells upon the end of fermentation was stably held at 20 to 40 million cells/ml, which was high and closer to that in normal fermentation. When the flocculent strain was used, by contrast, yeast was seen to sediment onto the upper part of carrier in the last half of fermentation, and the number of floating yeast cells upon the end of fermentation was 10 million cells/ml or less until the seventh fermentation process.

Here, when the number of yeast cells in the carrier was measured after 10 fermentation times, it was about $10^9$ cells/1 ml of carrier in each of the three strains, whereby it was verified that the number of immobilized yeast cells tolerable for practical use in a primary fermentation bioreactor was achieved in the non-flocculent strains as in the flocculent strain. When the state of yeast immobilized to the carrier was observed with an electronic microscope, it was verified that the non-flocculent strains were sufficiently immobilized in the chitosan type beads as with the flocculent strain. When the ratio of dead cells in and out of the carrier was investigated after 10 fermentation times, it was 10% or less in each of the three strains, whereby there was no problem.

TABLE 2

NUMBER OF FLOATING YEAST CELLS UPON THE END OF PRIMARY FERMENTATION (UNIT: $\times 10^6$ cells/ml)

NUMBER OF FERMENTATION TIMES

| | 1 | 2 | 3 | 4 | 5 | 6 | 7 | AVERAGE |
|---|---|---|---|---|---|---|---|---|
| NA-1 | 35 | 32 | 33 | 44 | 30 | 36 | 42 | 36.0 |
| NA-2 | 26 | 32 | 32 | 34 | 14 | 25 | 22 | 26.4 |
| A-1 | 5 | 7 | 9 | 5 | 8 | 7 | 11 | 7.4 |

Examples 3 and 4 and Comparative Example 2

Using the fluidized bed type bioreactor (total volume: 20 liters) shown in FIG. 1, the primary fermentation process was carried out by the above-mentioned repeated batch fermentation (repeated batch type) under the following conditions. Then, thus obtained fermentation liquid was subjected to a fermentative property test, a floating yeast cell counting test, and a diacetyl generated amount test which will be explained later.

Primary Fermentation Conditions

Carrier: chitosan type beads (Chitopearl HP manufactured by Fuji Spinning Co., Ltd.)

Scale: 6 L of carrier, 8 L of wort

Strains Used: A-2 (Comparative Example 1), NA-3 (Example 3), NA-4 (Example 4)

Yeast Immobilizing Method: Yeast is immobilized as being brought into contact with the carrier for 2 days while being circulated according to a conventional method (650 g of sludge yeast with respect to 6 L of carrier).

Liquid Space Velocity: 6 to 12 cm/min

Fermentation temperature: constantly 8° C.

Fermentation Time: 48 hours/batch

Batch number of Fermentation times: 7

Wort Used: wort adjusted to yield a sugar index of 11% Plato.

Fermentative Property Test

In each primary fermentation process, the amount of consumption of extract during 24 hours after starting fermentation determined by a vibration type densitometer (DMA58, manufactured by Anton Paar GmbH) was used as an index for fermentation rate comparison. Thus obtained results are shown in Table 3 and FIG. 3.

Figure 3:
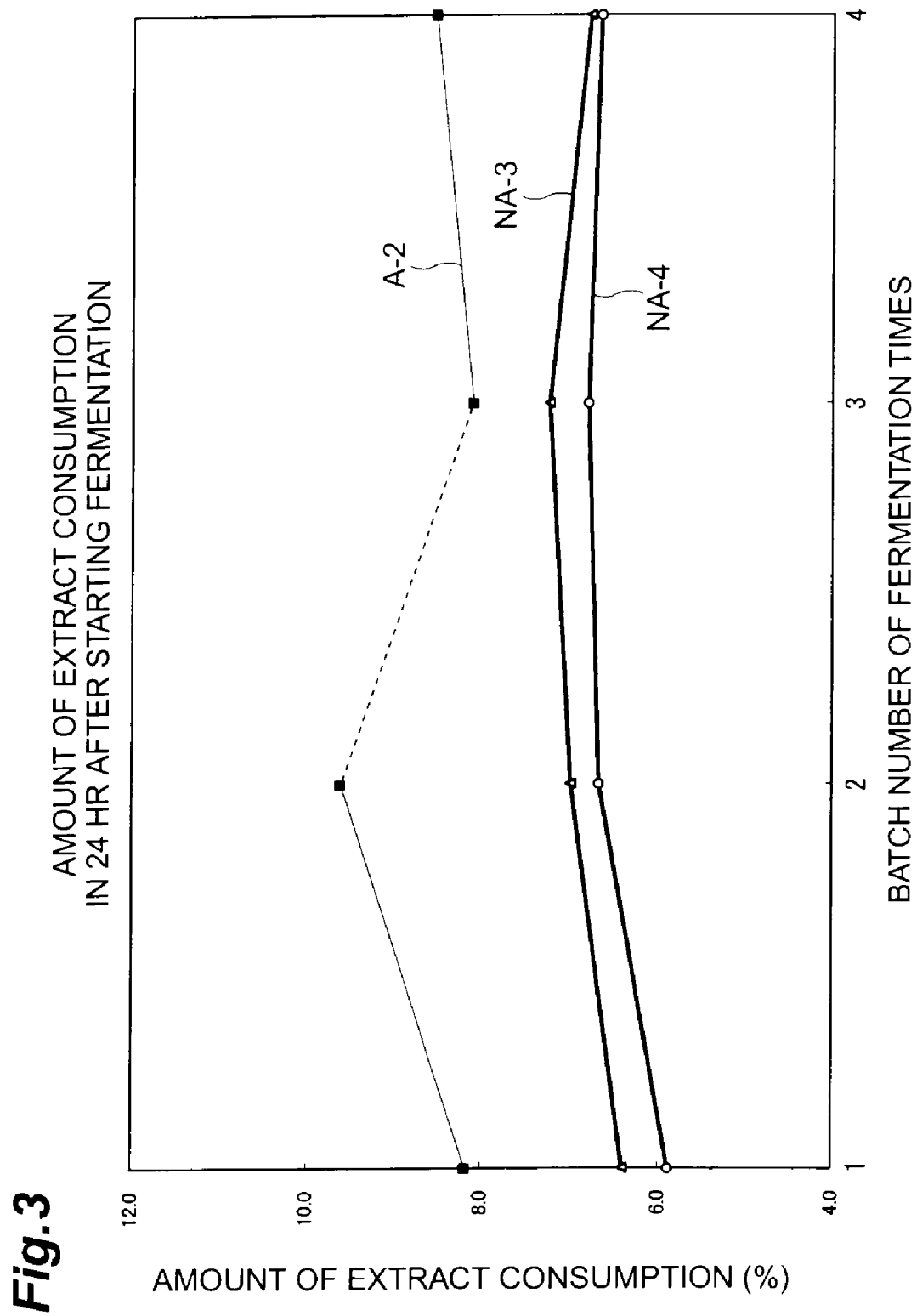
FIG. 3 is a graph showing relationships between the batch number of fermentation times and the amount of extract consumption.

As can be seen from the results shown in Table 3 and FIG. 3, the fermentation rate converged to substantially a constant value (about 6.7%/24 hr) at the first process and later in the case where the non-flocculent strains were used. The primary fermentation was completed in about 2 days. When the non-flocculent strains were used, no yeast was seen to precipitate in the reactor.

In the case where the flocculent strain was used, the flocculated and sedimented yeast tended to precipitate within the reactor vessel, so that the amount of yeast involved in fermentation increased, thereby accelerating the fermentation rate and making it inconstant. Here, the fermentation rate was slower in the third fermentation process than in the second fermentation process in the case where the flocculent strain was used, because of the fact that the precipitated yeast was removed by exchanging malts in a short period of time therebetween. Thus, the fermentation rate was hard to control when the flocculent strain was used, and it was necessary to carry out processing such as elimination of precipitated yeast in order to stabilize the fermentation rate.

TABLE 3

| NUMBER OF FERMENTATION | AMOUNT OF EXTRACT CONSUMPTION IN 24 HR AFTER STARTING FERMENTATION (%) | | | | |
|---|---|---|---|---|---|
| TIMES | 1 | 2 | 3 | 4 | AVERAGE |
| NA-3 | 6.4 | 7.0 | 7.2 | 6.8 | 6.8 |
| NA-4 | 5.9 | 6.7 | 6.8 | 6.6 | 6.5 |
| A-2[*1] | 8.2 | 9.6 | 8.1 | 8.5 | 8.6 |

[*1]In A-2, the inside of column was washed with wort (malt) between the second and third processes, so as to control the fermentation rate.

Floating Yeast Cell Counting Test

After the end of each fermentation process, the number of floating yeast cells in the fermentation liquid was counted in the same manner as Example 1. Thus obtained results are shown in Table 4 and FIG. 4.

Figure 4:
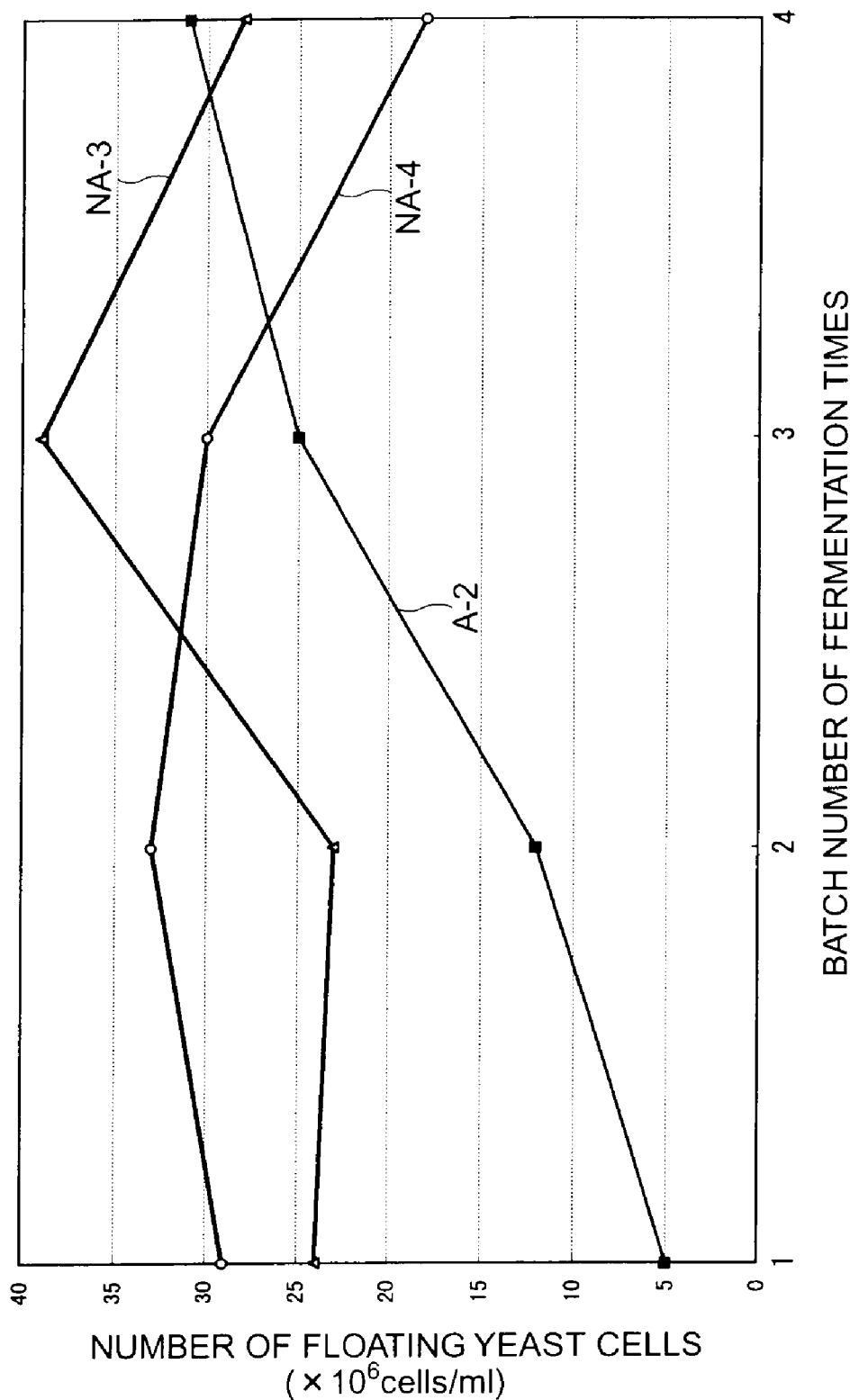
FIG. 4 is a graph showing relationships between the batch number of fermentation times and the number of floating yeast cells.

As can be seen from the results shown in Table 4 and FIG. 4, when non-flocculent strains were used under the above-mentioned conditions, the number of floating yeast cells upon the end of fermentation was stably held at high levels, i.e., 23 to 39 million cells/ml in NA-3, and 18 to 33 million cells/ml in NA-4. When the flocculent strain was used, by contrast, the number was 5 to 31 million cells/ml, and yeast was seen to sediment within the reactor in the last half of repeated batch fermentation, and the number of floating yeast cells upon the end of fermentation greatly fluctuated under the influence thereof.

TABLE 4

| NUMBER OF FERMENTATION | NUMBER OF FLOATING YEAST CELLS UPON THE END OF PRIMARY FERMENTATION ($10^6$ cells/ml) | | | | |
|---|---|---|---|---|---|
| TIMES | 1 | 2 | 3 | 4 | AVERAGE |
| NA-3 | 24 | 23 | 39 | 28 | 28.5 |
| NA-4 | 29 | 33 | 30 | 18 | 27.5 |
| A-2 | 5 | 12 | 25 | 31 | 18.3 |

Diacetyl Generated Amount Test

After the end of each primary fermentation process, the amount of generation of diacetyl (DA) in the fermentation liquid was measured by a gas chromatography (GC-14B, manufactured by Shimadzu Corp.). Thus obtained results are shown in Table 5 and FIG. 5.

Figure 5:
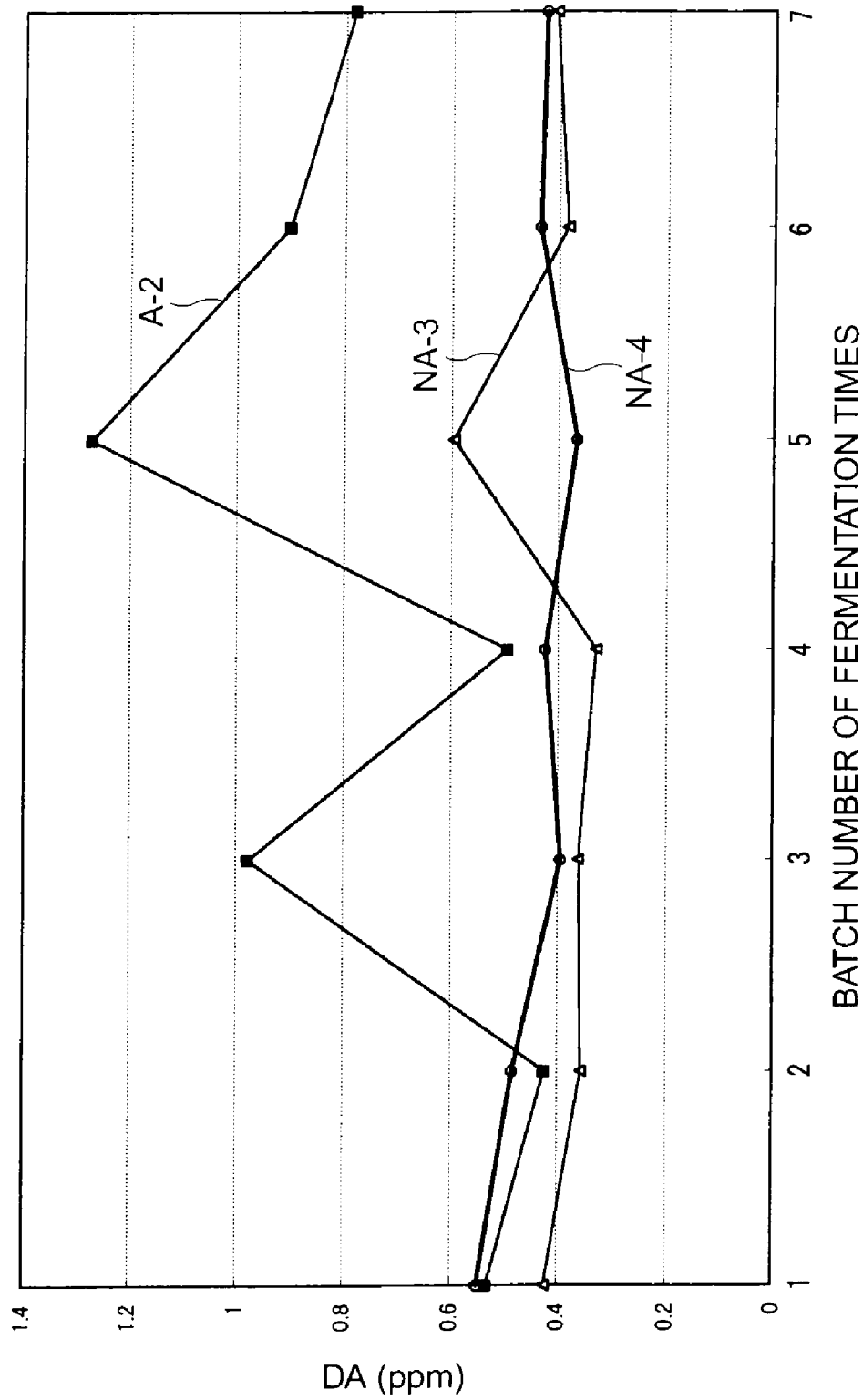
FIG. 5 is a graph showing relationships between the batch number of fermentation times and the amount of diacetyl.

As can be seen from the results shown in Table 5 and FIG. 5, the amount of generation of diacetyl upon the end of primary fermentation was stably maintained at a low level of 0.3 to 0.6 ppm when the non-flocculent strains were used. When the flocculent strain was used, by contrast, the amount was 0.4 to 1.3 ppm. It was seen that the amount of generation of diacetyl when the non-flocculent strains were used was about half that when the flocculent strains were used and was stably held at this low level.

TABLE 5

| | AMOUNT OF DA UPON THE END OF PRIMARY FERMENTATION (ppm) NUMBER OF FERMENTATION TIMES | | | | | | | |
|---|---|---|---|---|---|---|---|---|
| | 1 | 2 | 3 | 4 | 5 | 6 | 7 | AVERAGE[*2] |
| NA-3 | 0.42 | 0.36 | 0.36 | 0.33 | 0.60 | 0.38 | 0.41 | 0.41 |
| NA-4 | 0.55 | 0.49 | 0.39 | 0.42 | 0.37 | 0.44 | 0.42 | 0.44 |
| A-2 | 0.53 | 0.42 | 0.98 | 0.49 | 1.27 | 0.90 | 0.78 | 0.77 |

[*2]normal level: about 0.4 ppm

Example 5

Using the fluidized bed type bioreactor (total volume: 450 liters) shown in FIG. 1, the primary fermentation process was carried out by the above-mentioned repeated batch fermentation (repeated batch type) under the following conditions. Then, thus obtained fermentation liquid was subjected to a fermentative property test, a floating yeast cell counting test, and a diacetyl generated amount test by the same methods as mentioned above. Further, in this example, a flavor component test and an organoleptic test were carried out for the final product.

Primary Fermentation Conditions
Carrier: chitosan type beads (Chitopearl HP manufactured by Fuji Spinning Co., Ltd.)
Scale: 120 L of carrier, 170 L of wort
Strains Used: NA-5 (non-flocculent strain)
Yeast Immobilizing Method: About 13 kg of sludge yeast were immobilized as being brought into contact with 120 L of the carrier while being circulated according to a conventional method as in Examples 3 and 4.
Liquid Space Velocity: 6 to 12 cm/min
Fermentation temperature: constantly 8° C.
Fermentation Time: 48 hours/batch
Batch number of Fermentation times: 9
Wort Used: wort adjusted to yield a sugar index of 11% Plato.

| Secondary Fermentation Conditions | |
|---|---|
| Scale: | 30 L |
| Period: | 4 weeks |

Secondary Fermentation Temperature: 8 to 0° C.

Figure 6:
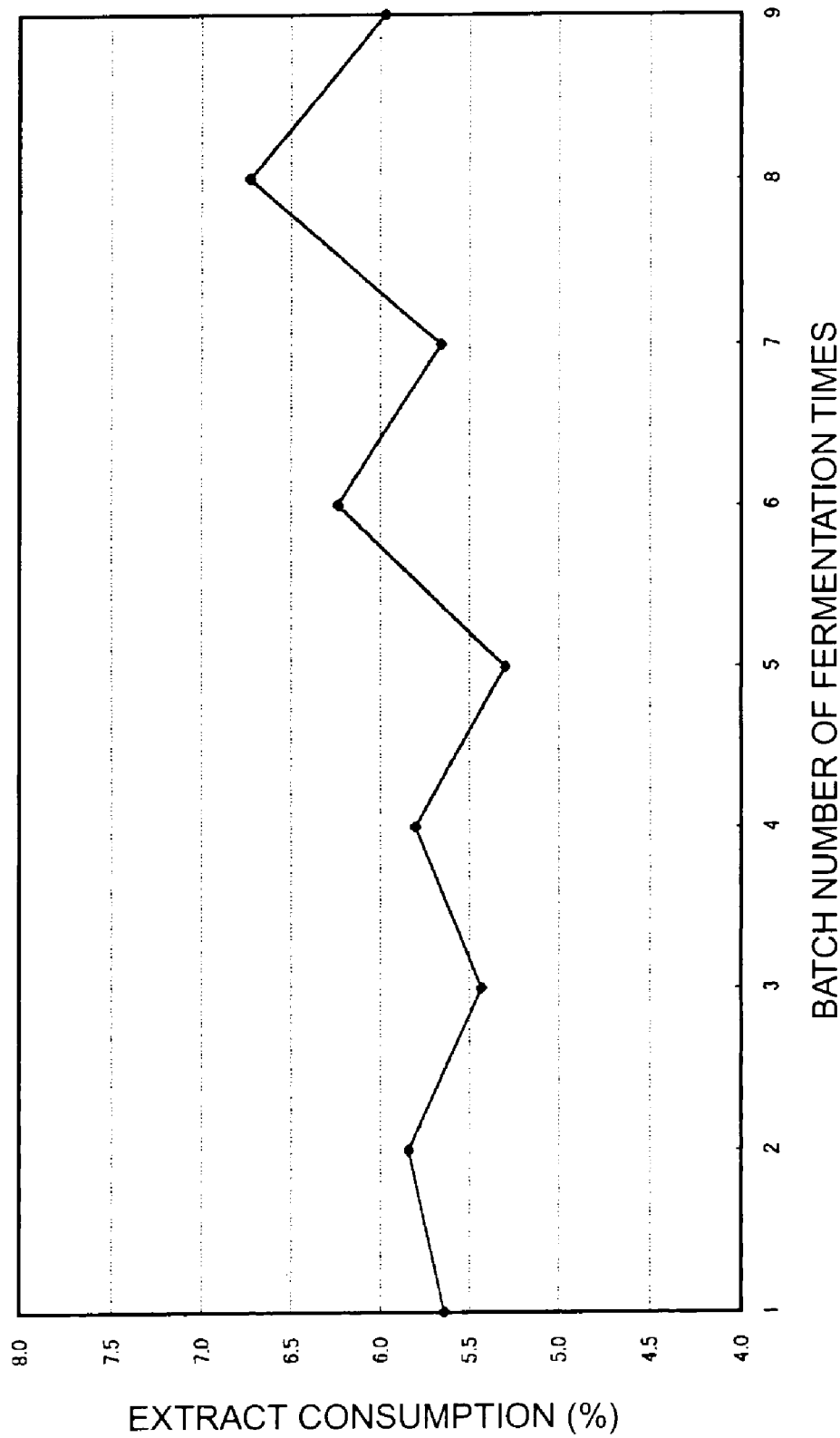
FIG. 6 is a graph showing a relationship between the batch number of fermentation times and the amount of extract consumption.

In the fermentative property test of this example, as can be seen from the results shown in Table 6 and FIG. 6, the fermentation rate after the completion of adaptation period became substantially a constant value (average value of about 5.8%/24 hr). The precipitation of yeast within the bioreactor, which is seen when flocculent strains are used, was not observed in this case as well.

TABLE 6

| | NUMBER OF FERMENTATION TIMES | | | | | | | | | |
|---|---|---|---|---|---|---|---|---|---|---|
| | 1 | 2 | 3 | 4 | 5 | 6 | 7 | 8 | 9 | AVERAGE |
| AMOUNT OF EXTRACT CONSUMPTION (%/24 HR) | 5.6 | 5.8 | 5.4 | 5.8 | 5.3 | 6.2 | 5.7 | 6.7 | 6.0 | 5.8 |

Figure 7:
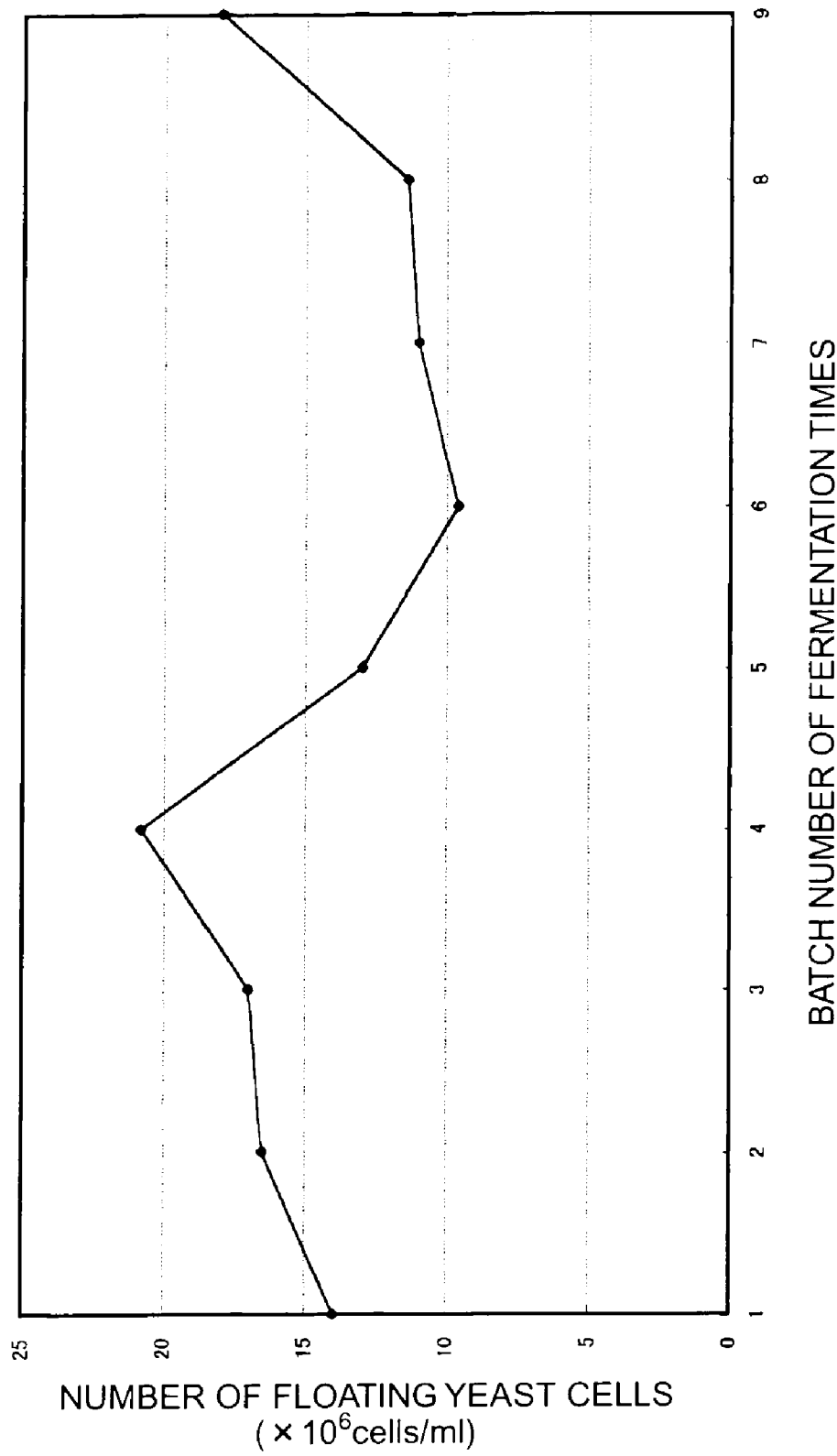
FIG. 7 is a graph showing a relationship between the batch number of fermentation times and the number of floating yeast cells.

In the floating yeast cell counting test of this example, as can be seen from the results shown in Table 7 and FIG. 7, the number was at a level of 10 to 20 million cells/ml (with an average value of about 15 million cells/ml), which was slightly lower than that in other examples using other smaller scale bioreactors, but it was possible for the number to be stably held at a level higher than a common level (3 to 10 million cells/ml) of the case where the flocculent strain was used in the 80-liter-scale bioreactor.

TABLE 7

| | NUMBER OF FERMENTATION TIMES | | | | | | | | | |
|---|---|---|---|---|---|---|---|---|---|---|
| | 1 | 2 | 3 | 4 | 5 | 6 | 7 | 8 | 9 | AVERAGE |
| NUMBER OF FLOATING YEAST CELLS (× 10$^6$ cells/ml) | 14 | 17 | 17 | 21 | 13 | 10 | 11 | 11 | 18 | 14.6 |

Figure 8:
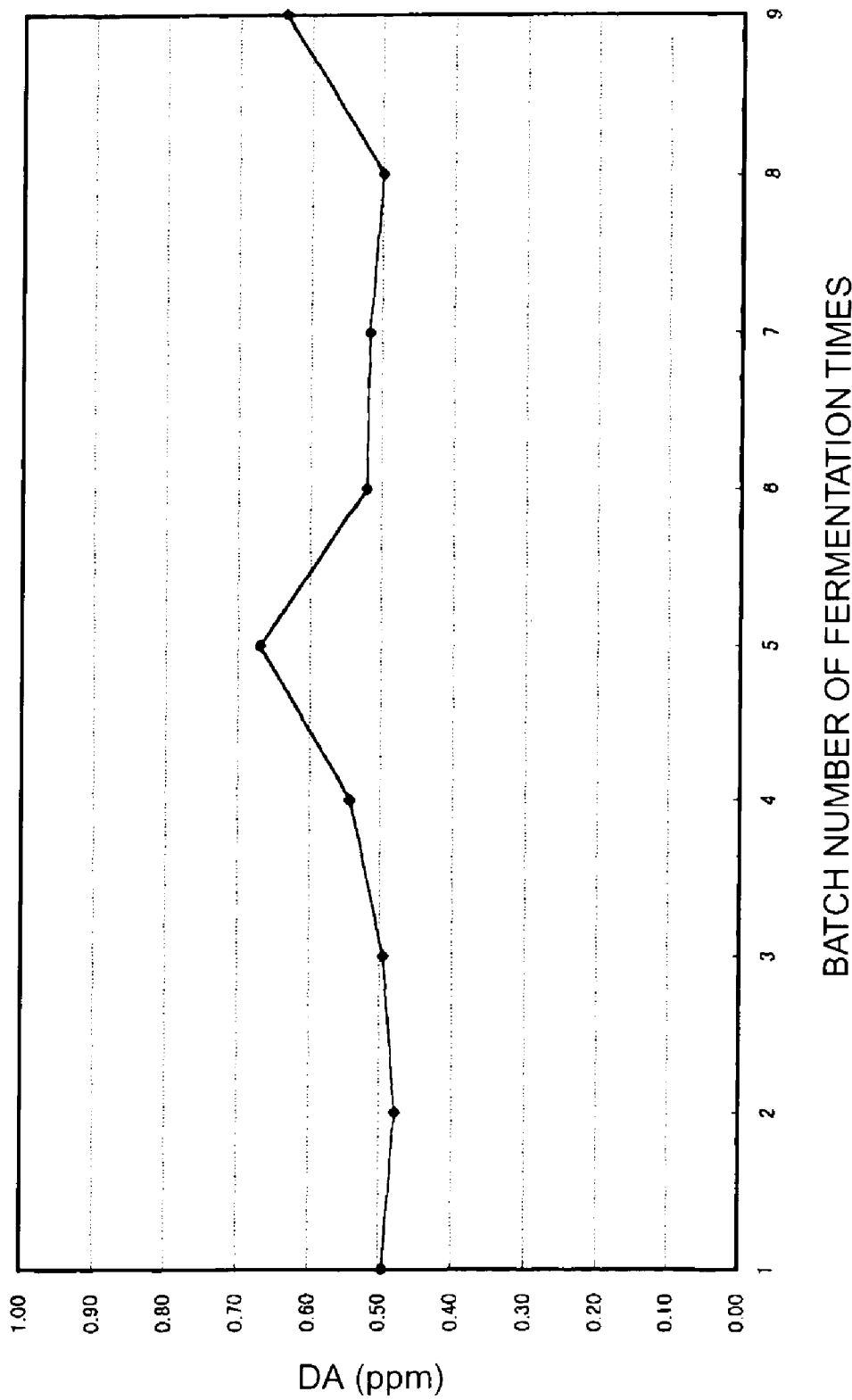
FIG. 8 is a graph showing a relationship between the batch number of fermentation times and the amount of diacetyl.

In the diacetyl generated amount test in this example, as can be seen from the results shown in Table 8 and FIG. 8, the amount of diacetyl generation upon the end of primary fermentation was 0.5 to 0.7 ppm (with an average value of about 5.8 ppm).

TABLE 8

| | NUMBER OF FERMENTATION TIMES | | | | | | | | | |
|---|---|---|---|---|---|---|---|---|---|---|
| | 1 | 2 | 3 | 4 | 5 | 6 | 7 | 8 | 9 | AVERAGE |
| DA (ppm) | 0.50 | 0.48 | 0.50 | 0.54 | 0.67 | 0.52 | 0.52 | 0.50 | 0.64 | 0.54 |

The beer having completed the primary fermentation in the bioreactor was subsequently subjected to secondary fermentation for 4 weeks at a scale of 30 liters. Thereafter, analyses of low volatile components (L.V.C.) and diacetyl, and an organoleptic test were carried out for the final product beer. The analysis of low volatile components was carried out with a gas chromatography GC4A manufactured by Shimadzu Corp.

Table 9 shows the results of analyses of low volatile components and diacetyl concerning the final product beer obtained by use of the beer yielded by the ninth primary fermentation. As can be seen from the results shown in Table 9, the final product beer obtained by this example was characterized in that the amount of acetate was higher than the analyzed value of that in a standard beer, whereas the amount of diacetyl, which might become problematic in bioreactor fermentation in particular, was reduced and lowered to 0.02 ppm, which was at a level hardly detectable organoleptically.

The results of a drinking test for the final product beer obtained in this example was not so different from those of conventional beers, and were favorable in general.

TABLE 9

| | ANALYSIS RESULT (ppm) | | | | | | | |
|---|---|---|---|---|---|---|---|---|
| | ACET-ALDEHYDE | ACETONE | ETHYL ACETATE | n-PrOH | i-BuOH | ISOAMYL ACETATE | i-AmOH | DA |
| REACTOR FERMENTATION | 4.3 | 0.1 | 36 | 14.6 | 12.7 | 2.0 | 56 | 0.02 |
| BEER STANDARD VALUE | 1.4 | 0.6 | 20 | 9.2 | 7.1 | 1.5 | 50 | 0.01 |

INDUSTRIAL APPLICABILITY

According to the method of the present invention, as explained in the foregoing, non-flocculent yeast is used contrary to the conventional knowledge when making a fermentation product by use of a bioreactor utilizing an immobilized microorganism, whereby the fermentation rate in the fermentation process can be held constant, and the number of floating yeast cells upon the end of fermentation can stably be maintained at a higher level.

When the method of the present invention is employed in the case of making a malt alcohol beverage by use of a bioreactor in particular, the amount of diacetyl in the fermentation liquid and final product can be lowered sufficiently and so forth, whereby the flavor of product can be improved.

The invention claimed is:

1. A method for making a fermentation product comprising:

immobilizing a non-flocculent yeast in a bioreactor, contacting a fermentation liquid with the immobilized non-flocculent yeast for a time and under conditions suitable for fermentation, and recovering the fermentation product(s),
wherein said non-flocculent yeast is immobilized on a carrier selected from the group consisting of a chitosan bead, alginic acid and carrageenan and
wherein said non-flocculent yeast satisfies the following:
a suspension of 0.6 g of said yeast is mixed with 20 ml of water,
1 ml of 0.5 M acetic acid buffer solution at pH 4.5 including 1,500 ppm calcium ion is added to 9 ml of said suspension,
the resulting mixture is left to stand still for 5 minutes at room temperature, and
neither flocculation nor sedimentation of said yeast is observed.

2. The method of claim 1, wherein said non-flocculent yeast is immobilized on a chitosan bead.

3. The method of claim 1, wherein said non-flocculent yeast is immobilized on alginic acid.

4. The method of claim 1, wherein said non-flocculent yeast is immobilized on carrageenan.

5. The method of claim 1, further comprising subjecting the fermentation products to a secondary fermentation.

6. The method of claim 1, wherein said non-flocculent yeast is a liquor yeast.

7. The method of claim 1, wherein said non-flocculent yeast is a beer yeast.

8. The method of claim 1, wherein said non-flocculent yeast is *Saccharomyces cerevisiae*.

9. The method of claim 1, wherein said non-flocculent yeast is *Saccharomyces uvarum*.

10. The method of claim 1, wherein said bioreactor comprises a complete mixed vessel reactor.

11. The method of claim 1, wherein said bioreactor comprises a packed bed reactor.

12. The method of claim 1, wherein said bioreactor comprises a film reactor.

13. The method of claim 1, wherein said bioreactor comprises a fluidized bed reactor.

14. The method of claim 1, wherein said bioreactor comprises a lateral reactor.

15. The method of claim 1, wherein said fermentation liquid comprises malt.

16. The method of claim 1, wherein said fermentation liquid comprises a fruit juice.

17. The method of claim 1, wherein said fermentation liquid comprises a sugar liquid.

18. The method of claim 1, wherein said fermentation liquid comprises a cereal saccharified liquid.

19. The method of claim 1, wherein said fermented product is beer.

20. The method of claim 1, wherein said fermented product is a malt alcohol beverage.

21. The method of claim 1, wherein said fermented product is sake.

22. The method of claim 1, wherein said fermented product is wine.

23. The method of claim 1, wherein said fermented product is vinegar.

24. The method of claim 1, wherein said fermented product is soy sauce.

25. A fermentation method comprising:
immobilizing a non-flocculent yeast on an immobilizing carrier within a bioreactor having a fluidized bed section,
supplying the bioreactor with a fermentation liquid,
extracting a part of the fermentation liquid from the downstream side of the fluidized bed section and returning the part of the fermentation liquid to the upstream side of the fluidized bed section, while forming a fluidized bed to carry out the fermentation of the fermentation liquid; and
recovering the thus obtained fermentation product from the bioreactor and
optionally supplying the bioreactor with a new fermentation liquid to repeat the fermentation,
wherein said non-flocculent yeast satisfies the following:
a suspension of 0.6 g of said yeast is mixed with 20 ml of water,
1 ml of 0.5 M acetic acid buffer solution at pH 4.5 including 1,500 ppm calcium ion is added to 9 ml of said suspension,
the resulting mixture is left to stand still for 5 minutes at room temperature, and
neither flocculation nor sedimentation of said yeast is observed.

26. The method of claim 25, wherein said non-flocculent yeast is immobilized on a carrier selected from the group consisting of a chitosan bead, alginic acid and carrageenan.

27. The method of claim 25, wherein the immobilizing carrier is a chitosan bead.

28. The method of claim 25, wherein the non-flocculent yeast is a non-flocculent liquor yeast and the fermentation product is a liquor.

29. The method of claim 25, wherein the non-flocculent yeast is a non-flocculent bear yeast and the fermentation product is a malt alcohol beverage.

30. A method for making a fermentation product comprising:
immobilizing a non-flocculent yeast in a fluidized bed bioreactor on the surface of a chitosan bead,
contacting a fermentation liquid with the immobilized non-flocculent yeast for a time and under conditions suitable for fermentation,
recovering the primary fermentation product(s),
wherein the primary fermentation product(s) have a higher number of floating yeast cells that the primary fermentation product(s) obtained using a similar flocculent yeast of the same species, and
wherein said non-flocculent yeast satisfies the following:
a suspension of 0.6 g of said yeast is mixed with 20 ml of water,
1 ml of 0.5 M acetic acid buffer solution at pH 4.5 including 1,500 ppm calcium ion is added to 9 ml of said suspension,
the resulting mixture is left to stand still for 5 minutes at room temperature, and
neither flocculation nor sedimentation of said yeast is observed.

* * * * *